United States Patent [19]
Elokdah et al.

[11] Patent Number: 5,877,324
[45] Date of Patent: *Mar. 2, 1999

[54] 2-(SUBSTITUTED SULFANYL)-3,5-DIHYDRO-IMIDAZOL-4-ONE DERIVATIVES

[75] Inventors: Hassan M. Elokdah, Yardley; Theodore S. Sulkowski, Wayne; Donald P. Strike, St. Davids, all of Pa.

[73] Assignee: American Home Products Corporation, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 754,441

[22] Filed: Nov. 21, 1996

Related U.S. Application Data

[60] Provisional application No. 60/007,653 Nov. 28, 1995.

[51] Int. Cl.$^6$ ................................. C07D 233/86
[52] U.S. Cl. .................... 548/319.1; 548/319.5; 548/320.5; 548/321.1
[58] Field of Search .............. 548/319.1, 319.5, 548/320.5, 321.1

[56] References Cited

U.S. PATENT DOCUMENTS

| | | |
|---|---|---|
| 5,137,904 | 8/1992 | Baran et al. . |
| 5,411,981 | 5/1995 | Gaillard-Kelly et al. . |
| 5,589,497 | 12/1996 | Claussner et al. ............ 548/321.1 |

FOREIGN PATENT DOCUMENTS

| | | |
|---|---|---|
| 0578516 | 1/1994 | European Pat. Off. . |
| 4887030 | of 1973 | Japan . |
| 4297461 | of 1992 | Japan . |
| 9420460 | 9/1994 | WIPO . |

OTHER PUBLICATIONS

Sauter et al, "[Bis(Methythio)Methylane], Etc" CA 123:228102, 1995.
Daboun et al, "Reactions of Amino Acids On 2–, Etc." CA 95:43024, 1981.
Scheiber, K.C., Chem Abst., vol. 49, No. 17, 11657h–11659a, Sep. 10, 1955.
Sauter et al., Heterocycles, 40(2) 851–866 (1995).
Harris et al., J. Med. Chem., vol. 35, 4384–4392 (1992).
Daboun, Z. Naturforsch., 866, 366–369 (1981).

*Primary Examiner*—Patricia L. Morris
*Attorney, Agent, or Firm*—Rebecca R. Barrett

[57] ABSTRACT

The compound of formula I:

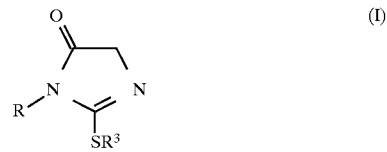

wherein R is phenyl or phenyl optionally substituted with one or more groups selected from halogen, alkyl, perfluoroalkyl, alkoxy, perfluoroalkoxy, hydroxy, alkanoyloxy, aroyloxy or arylalkanoyloxy; $R^3$ is alkyl, aryl or arylalkyl; or a pharmaceutically acceptable salt thereof, are use for increasing HDL blood levels.

16 Claims, No Drawings

2-(SUBSTITUTED SULFANYL)-3,5-DIHYDRO-IMIDAZOL-4-ONE DERIVATIVES

This application claims the benefit of U.S. application Ser. No. 60/007,653, filed Nov. 28, 1995.

BACKGROUND OF THE INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al, *Am. J. Med.,* 11 (1951) 480–493; Gofman et al, *Circulation,* 34 (1966) 679–697; Miller and Miller, *Lancet,* 1 (1975) 16–19; Gordon et al, *Circulation,* 79(1989) 8–15; Stampfer et al, *N. Engl. J. Med.,* 325 (1991) 373–381; Badimon et al, *Lab. Invest.,* 60 (1989) 455–461). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated level of some HDL particles in humans appears to be correlated to a decreased number of sites of stenosis in the coronary arteries of humans (Miller et al, *Br. Med. J.,* 282 (1981) 1741–1744).

There are several mechanisms by which HDL may protect against the progression of atherosclerosis. Studies in vitro have shown that HDL is capable of removing cholesterol from cells (Picardo et al, *Arteriosclerosis,* 6 (1986) 434–441). Data of this nature suggest that one antiatherogenic property of HDL may lie in its ability to deplete tissues of excess free cholesterol and eventually lead to the delivery of this cholesterol to the liver (Glomset, *J. Lipid Res.,* 9 (1968) 155–167). This has been supported by experiments showing efficient transfer of cholesterol from HDL to the liver (Glass et al, *Circulation,* 66 (Suppl. I) (1982) 102; MacKinnon et al, *J. Biol. Chem.,* 261 (1986) 2548–2552). In addition, HDL may serve as a reservoir in the circulation for apoproteins necessary for the rapid metabolism of triglyceride-rich lipoproteins (Grow and Fried, *J. Biol. Chem.,* 253 (1978) 1834–1841; Lagocki and Scanu, *J. Biol. Chem.,* 255 (1980) 3701–3706; Schaefer et al, *J. Lipid Res.,* 23 (1982) (1259–1273). Accordingly, agents which increase HDL cholesterol concentrations are useful as anti-atherosclerotic agents, particularly in the treatment of dyslipoproteinemias and coronary heart disease.

U.S. Pat. No. 5,411,981 discloses N-phenyl imidazolidines of the following formula (I) as anti-androgenic agents useful in the treatment of cancers of the breast, brain, ovaries, bladder, liver and kidney:

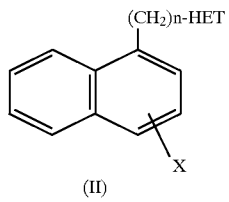

in which -A-B- is

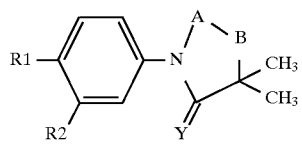

where $R^1$ is cyano, nitro or halogen; $R^2$ is trifluoromethyl or halogen; X is oxygen or sulfur, Y is oxygen, sulfur or nitrogen and $R^3$ is hydrogen or a vast variety of organic groups.

Related publication EP 578516 emphasizes compounds of formula Ia, with special emphasis on the 4-cyano-2-trifluoromethyl-phenyl group in each of the disclosed species.

WO 94/20460 discloses a genus of compounds of formula II as angiotensin-II receptor antagonists, useful for the treatment of hypertension, congestive heart failure, renal faillure and glaucoma.

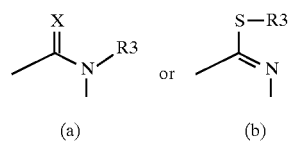
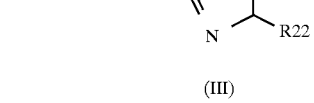

In the generic disclosure, HET represents numerous heterocycles, one of which is an imidazolidinone (III) in which R2 may be an 2–8 C alkylthio group among other things. There is no specific example of a compound disclosed in the document that corresponds with those variables. $R^{22}$ is a 3–4 membered polymethylene (spiro) group.

DESCRIPTION OF INVENTION

In accordance with this invention there is provided a group of 2-(substituted sulfanyl) dihydro-imidazolones of formula I,

wherein

R is phenyl or phenyl optionally substituted with one or more groups selected from halogen, alkyl of 1 to 6 carbon atoms, perfluoroalkyl of 1 to 6 carbon atoms, alkoxy of 1 to 6 carbon atoms, perfluoroalkoxy of 1 to 6 carbon atoms, hydroxy, alkanoyloxy of 2 to 6 carbon atoms, aroyloxy of 7 to 11 carbon atoms or arylalkanoyloxy of 8 to 16 carbon atoms;

$R^3$ is alkyl of 1 to 6 carbon atoms, aryl of 6 to 10 carbon atoms or arylalkyl of 7 to 12 carbon atoms;

or a pharmaceutically acceptable salt thereof.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids. The alkyl and alkoxy groups may be straight chain or branched chain, such as methyl, ethyl, propyl, isopropyl, butyl, isobutyl, tertiary butyl, pentyl, neopentyl, hexyl, methoxy, ethoxy, propoxy, butoxy, isobutoxy, hexyloxy, and the like.

A preferred group of compounds are those of formula I:

wherein

R is phenyl or phenyl optionally substituted with one or more groups selected from halogen, alkyl of 1 to 3 carbon atoms, perfluoromethyl, alkoxy of 1 to 3 carbon atoms, perfluoromethoxy, hydroxy or alkanoyloxy of 2 to 4 carbon atoms;

$R^3$ is alkyl of 1 to 3 carbon atoms or arylalkyl or 7 to 9 carbon atoms; or a pharmaceutically acceptable salt thereof.

The most preferred compounds of this invention are:

2-Ethylsulfanyl-3-(4-fluorophenyl)-3,5-dihydro-imidazol-4-one or a pharmaceutically acceptable salt thereof;

3-(5-Chloro-2-methylphenyl)-2-ethylsulfanyl-3,5-dihydro-imidazol-4-one or a pharmaceutically acceptable salt thereof;

3-(5-Chloro-2-methoxyphenyl)-2-ethylsulfanyl-3,5-dihydro-imidazol-4-one or a pharmaceutically acceptable salt thereof;

3-(2,6-Dichlorophenyl)-2-ethylsulfanyl-3,5-dihydro-imidazol-4-one or a pharmaceutically acceptable salt thereof;

2-Benzylsulfanyl-3-(5-chloro-2-methylphenyl)-3,5-dihydro-imidazol-4-one or a pharmaceutically acceptable salt thereof;

3-(2-Chlorophenyl)-2-ethylsulfanyl-3,5-dihydro-imidazol-4-one or a pharmaceutically acceptable salt thereof;

2-Ethylsulfanyl-3-(2-tolyl)-3,5-dihydro-imidazol-4-one or a pharmaceutically acceptable salt thereof;

3-(2-Chloro-6-methylphenyl)-2-ethylsulfanyl-3,5-dihydro-imidazol-4-one or a pharmaceutically acceptable salt thereof;

2-Ethylsulfanyl-3-phenyl-3,5-dihydro-imidazol-4-one or a pharmaceutically acceptable salt thereof;

3-(2,6-Dimethylphenyl)-2-ethylsulfanyl-3,5-dihydro-imidazol-4-one or a pharmaceutically acceptable salt thereof;

The compounds of this invention where $R^3$ is methyl (B) can be prepared by alkylation of 2-thioxo-imidazolidin-4-ones (A) with methyl iodide. The reaction proceeds in poor yield. The product is difficult to purify as a pharmaceutically acceptable salt. The alkylation has not been successfully carried out with alkyl iodides larger than methyl.

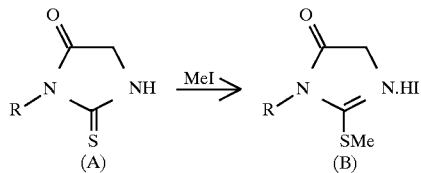

The compounds of the present invention are prepared according to the preferred general sequence of reactions outlined in the scheme below:

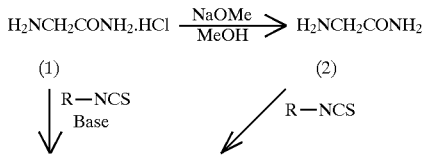

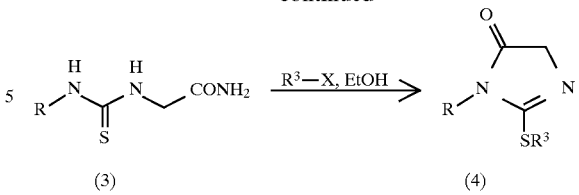

An amino acid amide hydrochloride (1) is converted to the base (2) with sodium methoxide in methanol. An appropriate isothiocyanate is added at room temperature to the amino acid amide in chloroform or methylene chloride. The mixture is heated to reflux, then heating is discontinued and stirring is continued for 20 minutes to 3 hours. The thiourea-amide (3) is isolated by standard procedures. In an alternative procedure, 3 can be obtained from the amino acid amide hydrochloride (1). In this procedure, 1 is reacted with an isothiocyanate in the presence of a base such as triethylamine. The thiourea-amide (3) is reacted with two equivalents of alkyl halide (or aryl halide) in ethanol at reflux for 2 to 5 hours. The ammonia that forms during cyclization effectively scavenges the hydrohalide formed during alkylation, allowing the title compounds (4) to be isolated as the free base. Desired salts can be prepared by standard methods.

This invention also provides pharmaceutical compositions comprised of 2-(substituted sulfanyl) dihydro-imidazol-4-ones either alone or in combination with excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 10 to about 200 milligrams/kilogram per day. However, in general, satisfactory results are indicated to be obtained at daily dosages in the range of from 400 milligrams to about 2000 milligrams, conveniently administered in divided doses two to four times a day.

The ability of the compounds of this invention to increase blood serum HDL levels was established by the following standard experimental procedure for determination of HDL cholesterol:

Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005–0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Sigma Procedure No. 352, modified for use with ninety-six well microtiter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25° C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 ul of serum is injected onto Superose 12 and Superose 6 (Pharmacia), in series, with a column buffer of 0.05M Tris (2-amino-2-hydroxymethyl-1,3-propanediol) and 0.15M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45° C. The eluent is monitored by measuring absorbance at 490 nm and gives a continuous absorbance signal proportional to the cholesterol concentration. The relative concentration of each lipoprotein class is calculated as the percent of total absorbance. HDL cholesterol concentration, in serum, is calculated as the percent of total cholesterol as determined by FPLC multiplied by the total serum cholesterol concentration.

The compounds of the present invention increase HDL cholesterol concentrations as summarized in Table I:

TABLE I

| Compound of Example | Dose (mg/kg/day) | Duration of Treatment (days) | HDL Cholesterol Level Increase (%) |
|---|---|---|---|
| 1 | 80 | 8 | 140 |
| 2 | 100 | 8 | 153 |
| 3 | 100 | 8 | 66 |
| 4 | 70 | 8 | 128 |
| 5 | 100 | 8 | 102 |
| 6 | 100 | 8 | 74 |
| 7 | 100 | 8 | 139 |
| 8 | 100 | 8 | 71 |
| 9 | 100 | 8 | 89 |
| 10 | 100 | 8 | 32 |
| 11 | 100 | 8 | 26 |
| 12 | 100 | 8 | 45 |
| 13 | 100 | 8 | 39 |
| 14 | 100 | 8 | 75 |

EXAMPLE 1

2-Ethylsulfanyl-3-(4-fluorolphenyl)-3,5-dihydro-imidazol-4-one

Glycinamide (5.0 g) and 4-fluorophenyl-isothiocyanate (9.18 g) were stirred in (200 mL). The mixture was heated at reflux for 5 minutes then stirred at ambient temperature for 20 minutes. The precipitated solid was collected by filtration, washed with chloroform and air dried to give 2-[3-(4-fluorophenyl)-thioureido]-acetamide (10.7 g) as a light pink solid, m.p. 168°–170° C. (dec.). Mass spectrum (EI, M.+) m/z 277. $^1$H-NMR (DMSO-$d_6$; 400 MHz) δ9.97 (broad s, 1 H), 7.82 (broad s, 1 H), 7.45–7.52 (m, 3 H), 7.10–7.17 (m, 3 H), and 4.06 ppm (s, 2 H).

A mixture of 2-[3-(4-fluorophenyl)-thioureido]-acetamide (9.1 g) and ethyl iodide (12.5 g) was heated at reflux in ethanol (200 mL) for 4 hours. The solvent was evaporated. The residue was dissolved in ethyl acetate (500 mL) then washed with water. The organic phase was extracted with 2N HCl (2×400 mL). The acid extract was made basic with 5% sodium bicarbonate solution. The precipitate was collected by filtration and dried. Crystallization from diethyl ether afforded the tide compound (2.85 g) as an off-white solid, m.p. 114°–115° C. Anal. Calcd. for. $C_{11} H_{11} F N_2 O S$: C, 55.45; H, 4.65; N, 11.76. Found: C, 55.17; H, 4.54; N,11.81. Mass spectrum (EI, M.$^+$) m/z 238. $^1$H-NMR (DMSO-$d_6$; 400 MHz) δ7.32–7.39 (m, 4 H), 4.30 (s, 2 H), 3.07 (q, 2 H), and 1.28 ppm (t, 3 H).

EXAMPLE 2
3-(5-Chloro-2-methylphenyl)-2-ethylsulfanyl-3,5-dihydro-imidazol-4-one Glycinamide (10.08 g) and 5-chloro-2-methylphenyl-isothiocyanate (23 g) were heated at reflux in chloroform (300 mL) for 30 minutes. The mixture was then stirred at ambient temperature for 3 hours. The precipitated solid was collected by filtration, washed with chloroform and air dried to give 2-[3-(5-chloro-2-methylphenyl)-thioureido]-acetamide (28.5 g), m.p. 162°–1640° C. Mass spectrum (EI, M.$^+$) m/z 257/259. $^1$H-NMR (DMSO-$d_6$; 400 MHz) δ9.46 (s, 1 H), 7.83 (s, 1 H), 7.51 (d, 2 H), 7.24 (d, 1 H), 7.24 (d, 1 H), 7.18 (d, 1 H), 7.15 (m, 2 H), 4.06 (d, 2 H), and 2.16 ppm (s, 3 H).

A mixture of 2-[3-(5-chloro-2-methylphenyl)-thioureido]-acetamide (25.8g) and ethyl iodide (32.0 g) was heated at reflux in ethanol (500 mL) for 5 hours. The solvent was evaporated. The residue was dissolved in ethyl acetate (500 mL) and water (300 mL). The organic phase was washed with water, dried over anhydrous MgSO$_4$, then evaporated to dryness. The residue was triturated with diethyl ether and the solid was collected by filtration and dried to give the title compound (17.0 g) as a yellow solid, m.p. 137°–139° C. Anal. Calcd. for. $C_{12} H_{13}$ Cl $N_2$ O S: C, 53.63; H, 4.88; N,10.42. Found: C, 53.58; H, 4.74; N, 10.32. Mass spectrum (EI, M.$^+$) m/z 268/270. $^1$H-NMR (DMSO-$d_6$; 400 MHz) δ7.45–7.49 (m, 1 H), 7.40–7.43 (m, 2 H), 4.35 (dd, 2 H), 3.07 (m, 2 H), 2.1 (s, 3 H), and 1.28 ppm (t, 3 H).

EXAMPLE 3
3-(5-Chloro-2-methoxyphenyl)-2-ethylsulfanyl-3,5-dihydro-imidazol-4-one A mixture of glycinamide hydrochloride (5.5 g), triethyl amine (5.05 g), 5-chloro-2-methoxyphenyl-isothiocyanate (9.95 g), and chloroform (500 mL) were heated at reflux for 3 hours. The mixture was then cooled to ambient temperature and washed with water (300 mL). The organic phase was separated. Precipitate formed upon standing. The solid was collected by filtration, washed with water, then with diethyl ether and air dried to give 2-[3-(5-chloro-2-methoxyphenyl)-thioureido]-acetamide (12.8 g), m.p. 166°–169° C. (dec.). This compound was used without further purification for the preparation of the title compound.

A mixture of 2-[3-(5-chloro-2-methoxyphenyl)-thioureido]-acetamide (11.0 g) and ethyl iodide (12.5 g) in ethanol (400 mL) was heated at reflux for 4.5 hours. The solvent was evaporated. The residue was dissolved in chloroform (500 mL) and washed with water. The organic phase was dried over anhydrous MgSO$_4$, then evaporated to dryness. The residue was crystallized from ethanol to give the title compound (6.1 g) as a tan solid, m.p. 113°–115° C. Anal. Calcd. for. $C_{12} H_{13}$ Cl $N_2$ $O_2$ S: C, 50.61; H, 4.60; N,9.84. Found: C, 50.32; H, 4.59; N, 9.77. Mass spectrum (ESI$^+$, [M+H]$^+$) m/z 285/287. $^1$H-NMR (DMSO-$d_6$; 400 MHz) δ7.53 (m, 1 H), 7.41 (d, 1 H), 7.22 (d, 1 H), 4.31 (dd, 2 H), 3.77 (s, 3 H), 3.05 (m, 2 H), and 1.26 ppm (t, 3 H).

EXAMPLE 4
3-(2,6-Dichlorophenyl)-2-ethylsulfanyl-3,5-dihydro-imidazol-4-one

2-[3-(2,6-Dichlorophenyl)-thioureido]-acetamide was prepared by the procedure described in Example 2 using 40.8 g of 2,6-dichlorophenyl-isothiocyanate and 29.6 g of glycinamide. The product was obtained (54 g) as a solid, m.p. 189°–191° C. Mass spectrum (+FAB, [M+H]$^+$) m/z 278/280/282. This intermediate was used in the next paragraph without further purification.

The title compound was prepared by the procedure described in Example 2 using 27.8 g of 2-[3-(2,6-dichlorophenyl)-thioureido]-acetamide and 31.2 g of ethyl iodide. 12.8 g of the title compound was obtained, m.p. 122°–124° C. Anal. Calcd. for. $C_{11} H_{10}$ $Cl_2$ $N_2$ O S: C, 45.69; H, 3.49; N, 9.69. Found: C, 45.62; H, 3.33; N, 9.43. Mass spectrum (+FAB, [M+H]$^+$) m/z 289/291/293. $^1$H-NMR (DMSO-$d_6$; 400 MHz) δ7.72 (s, 1 H), 7.70 (s, 1 H), 7.58 (t, 1 H), 4.50 (s, 2 H), 3.10 (q, 2 H), and 1.27 ppm (t, 3 H).

EXAMPLE 5
2-Benzylsulfanyl-3-(5-chloro-2-methylphenyl)-3.5-dihydro-imidazol-4-one A mixture of 2-[3-(5-chloro-2-methylphenyl)-thioureido]-acetamide (20.6 g), benzyl chloride (25.0 g), and ethanol (350 mL) was heated at reflux for 2.5 hours. The insolubles were removed by filtration and discarded. The filtrate was concentrated to one-half volume. Diethyl ether (300 mL) was added. The precipitated solid was separated by filtration and discarded. The filtrate was evaporated to dryness. The residue was dissolved in chloroform (300 mL) and washed with water. The organic phase was dried over anhydrous MgSO$_4$, decolorized on carbon then evaporated to dryness. The residue was triturated with diethyl ether to give the title compound (14.2 g) as an off-white solid, m.p. 140°–142° C. Anal. Calcd. for. $C_{17} H_{15}$ Cl $N_2$ O S: C, 61.72; H, 4.57; N, 8.47. Found: C, 61.62; H, 4.39; N, 8.37. Mass spectrum (EI, M.$^+$) m/z 330/332. $^1$H-NMR (DMSO-$d_6$; 400 MHz) δ7.46 (m, 1 H), 7.42 (m, 2 H), 7.38 (d, 2 H), 7.22–7.32 (m, 3 H), 4.31–4.48 (m, 4 H), and 2.06 ppm (s, 3 H).

EXAMPLE 6
3-(2-Chlorophenyl)-2-ethylsulfanyl-3,5-dihydro-imidazol-4-one

2-[3-(2-Chlorophenyl)-thioureido]-acetamide was prepared by the procedure described in Example 3 using 16.95 g of 2-chlorophenyl-isothiocyanate and equivalent amounts of all other reactants. 18.8 Grams of the desired product was obtained, m.p. 161°–163° C. Anal. Calcd. for. $C_9 H_{10}$ Cl $N_3$ O S: C, 44.35; H, 4.414; N, 17.24. Found: C, 43.99; H, 3.91; N, 17.12. Mass spectrum (+FAB, [M+H]$^+$) m/z 244/246. $^1$H-NMR (DMSO-$d_6$; 400 MHz) δ9.57 (s, 1 H), 8.06 (t, 1 H), 7.71 (d, 1 H), 7.52 (s, 1 H), 7.47 (m, 1 H), 7.28–7.32 (m, 1 H), 7.18–7.22 (m, 2 H), and 4.09 ppm (d, 2 H).

A mixture of 2-[3-(2-chlorophenyl)-thioureido]-acetamide (12.2 g), ethyl iodide (15.6 g), and ethanol (200 mL) was heated at reflux for 5 hours. The solvent was evaporated. The residue was dissolved in ethyl acetate (400 mL) and water (300 mL). The organic phase was washed with water (2×300 mL). The organic phase was then extracted with 2N HCl (2×500 mL). The acid extract was neutralized with solid sodium bicarbonate and extracted with ethyl acetate. The organic phase was washed with water, dried over anhydrous MgSO$_4$ then evaporated to dryness. The residue was dissolved in ethanol and the solution was saturated with hydrogen chloride. The solvent was evaporated and the residue was crystallized from ethyl acetate to give the hydrochloride salt of the title compound (8.4 g) as an off-white solid, m.p. 149°–150° C. (dec.). Anal. Calcd. for. $C_{11} H_{11} Cl N_2 O S \cdot HCl$: C, 45.37; H, 4.15; N, 9.62. Found: C, 44.97; H, 4.06; N, 9.51. Mass spectrum (EI, M.$^+$) m/z 254/256. $^1$H-NMR (DMSO-d$_6$; 400 MHz) δ7.69 (m, 1 H), 7.50–7.58 (m, 3 H), 4.45 (q, 2 H), 3.11–3.17 (m, 2 H), and 1.27 ppm (t, 3 H).

EXAMPLE 7
2-Ethylsulfanyl-3-(2-tolyl)-3,5-dihydro-imidazol-4-one

2-[3-(2-Tolyl)-thioureido]-acetamide was prepared by the procedure described in the first paragraph of Example 3 using 14.9 g of 2-tolyl-isothiocyanate and equivalent amounts of all other reactants. 17.1 Grams of product was obtained, m.p. 169°–171° C (dec.). This compound was used without further purification in the next paragraph.

The title compound was prepared by the procedure described in Example 6 using 11.2 g of 2-[3-(2-tolyl)-thioureido]-acetamide and 15.6 g of ethyl iodide. Crystallization from ethyl acetate afforded the hydrochloride salt of the title compound as a white solid (6.8 g), m.p. 156°–158° C. (dec.). Anal. Calcd. for. $C_{12} H_{14} N_2 O S \cdot HCl$: C, 53.23; H, 5.58; N, 10.34. Found: C, 52.96; H, 5.49; N, 10.25. Mass spectrum (EI, M.$^+$) m/z 234. $^1$H-NMR (DMSO-d$_6$; 400 MHz) δ8.75 (broad s, 2 H), 7.43 (m, 2 H), 7.35 (m, 1 H), 7.30 (m, 1 H), 4.53 (q, 2 H), 3.18–3.20 (m, 2 H), and 1.29 ppm (t, 3 H).

EXAMPLE 8
3-(2-Chloro-6-methylphenyl)-2-ethylsulfanyl-3,5-dihydro-imidazol-4-one 2-[3-(2-Chloro-6-methylphenyl)-thioureido]-acetamide was prepared by the procedure described in Example 2 using 18.3 g of 2-chloro-6-methylphenyl-isothiocyanate and 12.0 g of glycinamide. 22.8 Grams of the product was obtained, m.p. 161°–163° C. (dec.). This compound was used without further purification in the next paragraph.

The title compound was prepared by the procedure described in Example 6 using 12.9 g of 2-[3-(2-chloro-6-methylphenyl)-thioureido]-acetamide, and 18.0 g of ethyl iodide. The hydrochloride salt was prepared in ethereal hydrogen chloride. Crystallization from ethyl acetate afforded the title compound as the mono-hydrochloride as a light yellow solid (4.9 g), m.p. 152°–154° C. (dec.). Anal. Calcd. for. $C_{12} H_{13} Cl N_2 O S \cdot HCl$: C, 47.22; H, 4.62; N, 9.18. Found: C, 46.99; H, 4.60; N, 9.16. Mass spectrum (+FAB, [M+H]$^+$) m/z 269/271. $^1$H-NMR (DMSO-d$_6$; 400 MHz) δ8.28 (broad s, 2 H), 7.51 (m, 1 H), 7.44 (t, 1 H), 7.39 (m, 1 H), 4.51 (q, 2 H), 3.12 (q, 2 H), 2.17 (s, 3 H), and 1.27 ppm (t, 3 H).

EXAMPLE 9
2-Ethylsulfanyl-3-phenyl-3,5-dihydro-imidazol-4-one

A mixture of glycinamide hydrochloride (8.25 g), triethyl amine (10.0 g), phenyl-isothiocyanate (10.1 g), and methylene chloride (300 mL) was heated at reflux for 1 hour. The mixture was stirred at ambient temperature for 2 hours. The precipitate was collected by filtration, washed with methylene chloride, then with diethyl ether and air dried to give 2-(3-phenyl-thioureido)-acetamide (9.7 g), m.p. 150°–152° C. Anal. Calcd. for. $C_9 H_{11} N_3 O S$: C, 51.66; H, 5.30; N, 20.08. Found: C, 51.41; H, 5.04; N, 20.02. Mass spectrum (EI, M.$^+$) m/z 209. $^1$H-NMR (DMSO-d6; 400 MHz) δ9.88 (s, 1 H), 7.70 (t, 1 H), 7.52 (s, 1 H), 7.47 (d, 2 H), 7.31 (t, 2 H), 7.15 (s, 1 H), 7.09 (t, 1 H), and 4.08 ppm (d, 2 H).

A mixture of 2-(3-phenyl-thioureido)-acetamide (7.1 g), ethyl iodide (18.0 g), and ethanol (300 mL) was heated at reflux for 2 hours. The solvent was evaporated. The residue was dissolved in chloroform (300 mL) and water (300 mL). The organic phase was washed with water, dried over anhydrous MgSO$_4$, then evaporated to dryness. The residue was crystallized from ethyl acetate/hexane to give the title compound (3.1 g), m.p. 79°–81° C. Anal. Calcd. for. $C_{11} H_{12} N_2 O S$: C, 59.97; H, 5.49; N, 12.72. Found: C, 59.67; H, 5.35; N, 12.70. Mass spectrum (EI, M.$^+$) m/z 220. $^1$H-NMR (DMSO-d$_6$; 400 MHz) δ7.43–7.52 (m, 3 H), 7.28–7.31 (m, 2 H), 4.32 (s, 2 H), 3.07 (q, 2 H), and 1.27 ppm (t, 3 H).

EXAMPLE 10
2-Ethylsulfanyl-3-(5-fluoro-2-methylphenyl)-3,5-dihydro-imidazol-4-one A mixture of glycinamide hydrochloride (4.42 g), 5-fluoro-2-methylphenyl-isothiocyanate (6.68 g), triethyl amine (4.1 g), and chloroform (150 mL) was stirred at ambient temperature for 18 hours. The precipitate was collected by filtration, washed with chloroform and air dried to give 2-[3-(5-Fluoro-2-methylphenyl)-thioureido]-acetamide (7.6 g), m.p. 172°–174° C. (dec.). This compound was used without further purification in the next paragraph.

A mixture of 2-[3-(5-fluoro-2-methylphenyl)-thioureido]-acetamide (6.0 g), ethyl iodide (15.6 g), and ethanol (120 mL) was heated at reflux for 4 hours. The solvent was evaporated. The residue was treated with ethyl acetate (400 mL) and filtered. The filtrate was washed with water (300 mL). The organic phase was evaporated to dryness. The residue was dissolved in ethanol. The solution was saturated with hydrogen chloride. The solvent was evaporated and the residue was crystallized from ethyl acetate and dried under vacuum to give the mono-hydrochloride of the title compound as a white solid (4.2 g), m.p. 181°–183° C. Anal. Calcd. for. $C_{12} H_{13} F N_2 O S \cdot HCl$: C, 49.91; H, 4.89; N, 9.70. Found: C, 49.83; H, 4.82; N, 9.71. Mass spectrum (+FAB,[M+H]$^+$) m/z 253. $^1$H-NMR (DMSO-d$_6$; 400 MHz) δ7.50–8.45 (broad s, 2 H), 7.45 (m, 1 H), 7.27–7.34 (m, 2 H), 4.48 (q, 2 H), 3.21 (m, 2 H), 2.10 (s, 3 H), and 1.29 ppm (t, 3 H).

EXAMPLE 11
3-(3-Chloro-2-methylphenyl)-2-ethylsulfanyl-3,5-dihydro-imidazol-4-one A mixture of glycinamide hydrochloride (6.1 g), 3-chloro-2-methylphenyl-isothiocyanate (10.1 g), triethyl amine (5.6 g), and chloroform (200 mL) was heated at reflux for 3 hours then cooled to ambient temperature. The precipitate was collected by filtration, washed with chloroform and air dried to give 2-[3-(3-chloro-2-methylphenyl)-thioureido]-acetamide (12.5 g), m.p. 162°–164° C. (dec.). This compound was used without further purification for the preparation of the title compound of step 2.

The title compound was prepared by the procedure described in Example 6 using 12.0 g of 2-[3-(3-chloro-2-methylphenyl)-thioureido]-acetamide, and 25.0 g of ethyl iodide. The hydrochloride salt was prepared in ethereal hydrogen chloride. Crystallization from ethyl acetate afforded the title compound as a white solid, mono-hydrochloride (5.1 g), m.p. 161°–163° C. (dec.). Anal. Calcd. for. $C_{12} H_{13} Cl N_2 O S \cdot HCl$: C, 47.22; H, 4.62; N, 9.18. Found: C, 47.03; H, 4.40; N, 9.09. Mass spectrum (+FAB, [M+H]$^+$) m/z 269/271. $^1$H-NMR (DMSO-d$_6$; 400 MHz) δ9.05–9.85 (broad s, 2 H), 7.62 (d, 1 H), 7.39 (t, 1 H), 7.33 (d, 1 H), 4.48 (q, 2 H), 3.20 (m, 2 H), 2.15 (s, 3 H), and 1.29 ppm (t, 3 H).

EXAMPLE 12

3-(3-Chloro-4-methylphenyl)-2-ethylsulfanyl-3,5-dihydro-imidazol-4-one

2-[3-(3-Chloro-4-methylphenyl)-thioureido]-acetamide was prepared by the procedure described Example 11 using 18.36 g of 3-chloro-4-methylphenyl-isothiocyanate, 11.05 g of glycinamide hydrochloride, 10.1 g of triethyl amine, and 300 mL of chloroform. 22.0 Grams of the desired product was obtained, m.p. 167°–169° C. (dec.). Mass spectrum (EI, M.$^+$) m/z 257/259. $^1$H-NMR (DMSO-d$_6$; 400 MHz) δ9.93 (s, 1 H), 7.80 (t, 1 H), 7.73 (s, 1 H), 7.52 (s, 1 H), 7.25 (m, 2 H), 7.16 (s, 1 H), 4.07 (d, 2 H), and 2.27 ppm (s, 3 H).

A mixture of 2-[3-(3-chloro-4-methylphenyl)-thioureido]-acetamide (10.0 g), ethyl iodide (17.5 g), and ethanol (200 mL) was heated at reflux for 2.5 hours. The solvent was evaporated. The residue was dissolved in ethyl acetate (500 mL) and water (500 mL). The organic phase was washed with water (2×300 mL). The organic phase was extracted with 2N HCl (2×500 mL). The acid extract was neutralized with solid sodium bicarbonate and extracted with ethyl acetate. The organic phase was washed with water, dried over anhydrous Na$_2$SO$_4$ then evaporated to dryness. The residue was stirred in diethyl ether and filtered to give the title compound (8.4 g) as a white solid, m.p. 133°–135° C. Anal. Calcd. for. C$_{12}$ H$_{13}$ Cl N$_2$ O S: C, 53.63; H, 4.88; N,10.42. Found: C, 53.66; H, 4.78; N, 10.39. Mass spectrum (EI, M.$^+$) m/z 268/270. $^1$H-NMR (DMSO-d$_6$; 400 MHz) δ7.47 (d, 1 H), 7.43 (d, 1 H), 7.20 (dd, 1 H), 4.29 (s, 2 H), 3.07 (q, 2 H), 2.36 (s, 3 H), and 1.28 ppm (t, 3 H).

EXAMPLE 13

3-(4-Chloro-2-methylphenyl)-2-ethylsulfanyl-3,5-dihydro-imidazol-4-one

2-[3-(4-Chloro-2-methylphenyl)-thioureido]-acetamide was prepared by the procedure described in Example 11 using 18.36 g of 4-chloro-2-methylphenyl-isothiocyanate, 11.05 g of glycinamide hydrochloride, 10.1 g of triethyl amine, and 300 mL of chloroform. 21.4 Grams of the desired compound was obtained, m.p. 170°–172° C. (dec.). Mass spectrum (EI, M.$^+$) m/z 257/259. $^1$H-NMR (DMSO-d$_6$; 400 MHz) δ9.38 (s, 1 H), 7.62 (broad s, 1 H), 7.45 (s, 1 H), 7.35 (d, 1 H), 7.32 (d, 1 H), 7.21 (m, 1 H), 7.12 (s, 1 H), 4.06 (d, 2 H), and 2.17 ppm (s, 3 H).

The tide compound was prepared by the procedure described in Example 6 using 18.0 g of 2-[3-(4-chloro-2-methylphenyl)-thioureido]-acetamide, and 25.0 g of ethyl iodide. The hydrochloride salt was prepared in ethereal hydrogen chloride. Crystallization from ethyl acetate afforded the tide compound as an off-white solid, monohydrochloride (17.6 g), m.p. 166°–168° C. (dec.). Anal. Calcd. for. C$_{12}$ H$_{13}$ Cl N$_2$ O S . HCl: C, 47.22; H, 4.62; N, 9.18. Found: C, 47.24; H, 4.45; N, 9.05. Mass spectrum (+FAB, [M+H]$^+$) m/z 269/271. 1H-NMR (DMSO-d$_6$; 400 MHz) δ9.05–9.78 (broad s, 2 H), 7.53 (m, 1 H), 7.44 (d, 1 H), 7.41 (d, 1 H), 7.33 (d, 1 H), 4.48 (q, 2 H), 3.20 (m, 2 H), 2.13 (s, 3 H), and 1.29 ppm (t, 3 H).

EXAMPLE 14

3-(2.6-Dimethylphenyl)-2-ethylsulfanyl-3,5-dihydro-imidazol-4-one

A mixture of 2,6-dimethylphenyl-isothiocyanate (16.3 g), glycinamide hydrochloride (11.05 g), triethyl amine (12.0 g), and chloroform (250 mL) was heated at reflux for 3 hours. The solvent was evaporated. The residue was dissolved in ethyl acetate (500 mL) and washed with 1N HCl (300 mL) then with water (300 mL). The organic phase was evaporated to dryness, then the residue was stirred with diethyl ether. The solid was collected by filtration and dried to afford 2-[3-(2,6-dimethylphenyl)-thioureido]-acetamide as a solid (18.3 g). Mass spectrum (EI, M.$^+$) m/z 237. This compound was used without further purification in the preparation of the title compound.

The title compound was prepared by the procedure described in Example 12 using 8.0 g of 2-[3-(2,6-dimethylphenyl)-thioureido]-acetamide, 25.0 g of ethyl iodide, and (200 mL) ethanol. Crystallization from hexane/diethyl ether mixture afforded the title compound as a light yellow solid (2.4 g), m.p. 86°–88° C. Anal. Calcd. for. C$_{12}$ H$_{16}$ N$_2$ O S: C, 62.87; H, 6.49; N, 11.28. Found: C, 62.98; H, 6.57; N, 11.30. Mass spectrum (El, M.$^+$) m/z 248. $^1$H-NMR (DMS-d$_6$; 400 MHz) δ7.27–7.30 (m, 1 H), 7.21 (m, 1 H), 7.19 (m, 1 H), 7.33 (d, 1 H), 4.42 (s, 2 H), 3.06 (q, 2 H), 2.07 (s, 6H), and 1.26 ppm (t, 3 H).

What is claimed is:

1. A compound of formula I:

wherein

R is phenyl or phenyl optionally substituted with one or more groups selected from halogen, alkyl of 1 to 6 carbon atoms, perfluoroalkyl of 1 to 6 carbon atoms, alkoxy of 1 to 6 carbon atoms, perfluoroalkoxy of 1 to 6 carbon atoms, hydroxy, alkanoyloxy of 2 to 6 carbon atoms, aroyloxy of 7 to 11 carbon atoms or arylalkanoyloxy of 8 to 16 carbon atoms;

R$^3$ is alkyl of 1 to 6 carbon atoms, aryl of 6 to 10 carbon atoms or arylalkyl of 7 to 12 carbon atoms; with the proviso that when R$^3$ is methyl, R is substituted phenyl; or a pharmaceutically acceptable salt thereof.

2. A compound of formula I:

wherein

R is phenyl or phenyl optionally substituted with one or more groups selected from halogen, alkyl of 1 to 3 carbon atoms, perfluoromethyl, alkoxy of 1 to 3 carbon atoms, perfluoromethoxy, hydroxy or alkanoyloxy of 2 to 4 carbon atoms;

R$^3$ is alkyl of 1 to 3 carbon atoms or arylalkyl or 7 to 9 carbon atoms; with the proviso that when R$^3$ is methyl, R is substituted phenyl; or a pharmaceutically acceptable salt thereof.

3. The compound of claim 1 which is 2-ethylsulfanyl-3-(4-fluorophenyl)-3,5-dihydro-imidazol-4-one or a pharmaceutically acceptable salt thereof.

4. The compound of claim 1 which is 3-(5-chloro-2-methylphenyl)-2-ethylsulfanyl-3,5-dihydro-imidazol-4-one or a pharmaceutically acceptable salt thereof.

5. The compound of claim 1 which is 3-(5-chloro-2-methoxyphenyl)-2-ethylsulfanyl-3,5-dihydro-imidazol-4-one or a pharmaceutically acceptable salt thereof.

6. The compound of claim 1 which is 3-(2,6-dichlorophenyl)-2-ethylsulfanyl-3,5-dihydro-imidazol-4-one or a pharmaceutically acceptable salt thereof.

7. The compound of claim 1 which is 2-benzylsulfanyl-3-(5-chloro-2-methylphenyl)-3,5-dihydro-imidazol-4-one or a pharmaceutically acceptable salt thereof.

8. The compound of claim 1 which is 3-(2-chlorophenyl)-2-ethylsulfanyl-3,5-dihydro-imidazol-4-one or a pharmaceutically acceptable salt thereof.

9. The compound of claim 1 which is 2-ethylsulfanyl-3-(2-tolyl)-3,5-dihydro-imidazol-4-one or a pharmaceutically acceptable salt thereof.

10. The compound of claim 1 which is 3-(2-chloro-6-methylphenyl)-2-ethylsulfanyl-3,5-dihydro-imidazol-4-one or a pharmaceutically acceptable salt thereof.

11. The compound of claim 1 which is 2-ethylsulfanyl-3-phenyl-3,5-dihydro-imidazol-4-one or a pharmaceutically acceptable salt thereof.

12. The compound of claim 1 which is 3-(2,6-dimethylphenyl)-2-ethylsulfanyl-3,5-dihydro-imidazol-4-one or a pharmaceutically acceptable salt thereof.

13. A compound of claim 1 which is 2-ethylsulfanyl-3-(5-fluoro-2-methylphenyl)-3,5-dihydro-imidazol-4-one or a pharmaceutically acceptable salt thereof.

14. A compound of claim 1 which is 3-(3-chloro-2-methylphenyl)-2-ethylsulfanyl-3,5-dihydro-imidazol-4-one or a pharmaceutically acceptable salt thereof.

15. A compound of claim 1 which is 3-(3-chloro-4-methylphenyl)-2-ethylsulfanyl-3,5-dihydro-imidazol-4-one or a pharmaceutically acceptable salt thereof.

16. A compound of claim 1 which is 3-(4-chloro-2-methylphenyl)-2-ethylsulfanyl-3,5-dihydro-imidazol-4-one or a pharmaceutically acceptable salt thereof.

* * * * *